US006770368B2

(12) United States Patent
Luhn

(10) Patent No.: US 6,770,368 B2
(45) Date of Patent: Aug. 3, 2004

(54) GRANULES BASED ON STARCH AND LACTOSE

(75) Inventor: Oliver Luhn, Wasserburg (DE)

(73) Assignee: Roquette Freres, Lestrem (FR)

( * ) Notice: Subject to any disclaimer, the term of this patent is extended or adjusted under 35 U.S.C. 154(b) by 32 days.

(21) Appl. No.: 09/905,569

(22) Filed: Jul. 13, 2001

(65) Prior Publication Data

US 2002/0035248 A1 Mar. 21, 2002

(30) Foreign Application Priority Data

Jul. 27, 2000 (EP) .............................................. 00402159

(51) Int. Cl.$^7$ .............................................. B32B 19/00
(52) U.S. Cl. ...................................... 428/403; 424/489
(58) Field of Search .......................... 428/403; 424/489, 424/498

(56) References Cited

U.S. PATENT DOCUMENTS 5,006,345 A    4/1991  Lang
5,618,562 A  * 4/1997  Saito et al. .................. 424/488

FOREIGN PATENT DOCUMENTS

GB         833458      4/1960
GB         2093052     8/1982

OTHER PUBLICATIONS

Hill PM: "Starch Paste Granulations_" Journal of Pharmaceutical Sciences, vol. 65, No. 2, 1976, pp. 313–314.
Tadashi Makino et al : "Importance of Gelatinization Degree of Starch Past . . . " Chemical and Pharmaceutical Bulletin, JP, vol. 13, No. 3, Mar. 1, 1995, pp. 514–516.
Visavarungroj N et al : "Crosslinked Starch as Binding Agent I. Conventional Wet Granulation" International Journal of Pharmaceutics, vol. 59, No. 1, 1990, pp. 73–78.
M.O. Bode–Tunji and K.T. Jaiyeoba : The effect of starch and surfactants on the granulation of soluble and insoluble powders, 1984, p. 190–192.
L.S.C. Wan and K.D Lim : "Granulation of mixtures of lactose and starch by a fluidized bed technique", 1991, p 285–293.
A. Stamm and C. Mathis : "Les excipients pour compression directe", 1976, p 237–246.
Extrait de la pharmacopee, 1997, p 1111–1112.

* cited by examiner

Primary Examiner—Thurman K. Page
Assistant Examiner—Robert M. Joynes
(74) Attorney, Agent, or Firm—Sturm & Fix LLP

(57) ABSTRACT

The invention concerns granules consisting of lactose and starch having a friability of less than or equal to 80%, preferably to 60%, according to a test A.

It also concerns the process of preparation of such granules as well as their use for the preparation of solid forms in the pharmaceutical or in the food industries.

11 Claims, 4 Drawing Sheets

75 LACTOSE / 25 STARCH
MAGNIFICATION: X 85

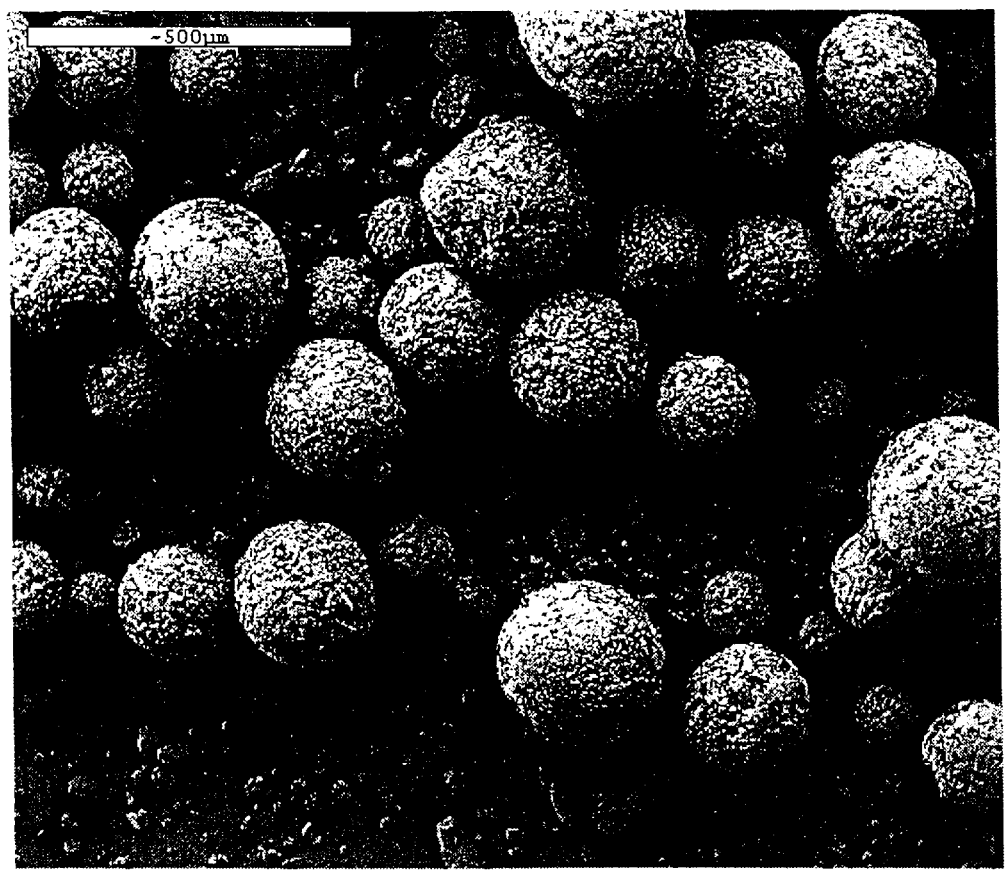
Figure 1 : 75 LACTOSE / 25 STARCH
MAGNIFICATION : X 85

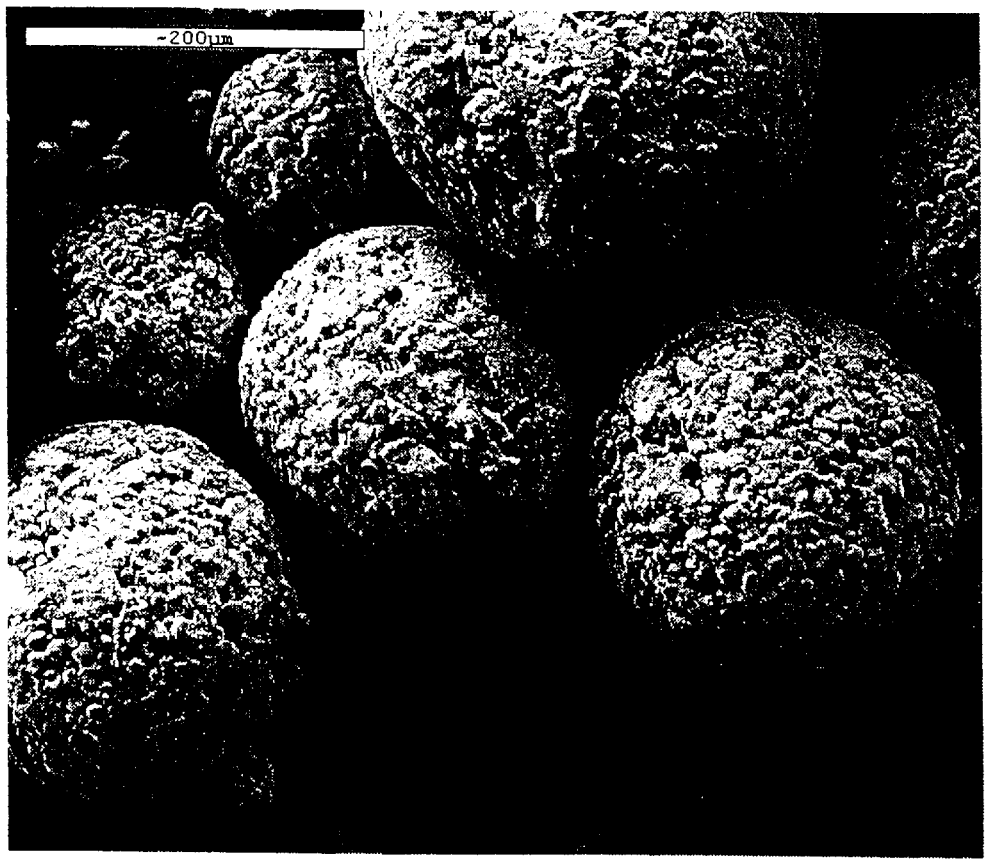
Figure 1' : 75 LACTOSE / 25 STARCH
MAGNIFICATION: X 225

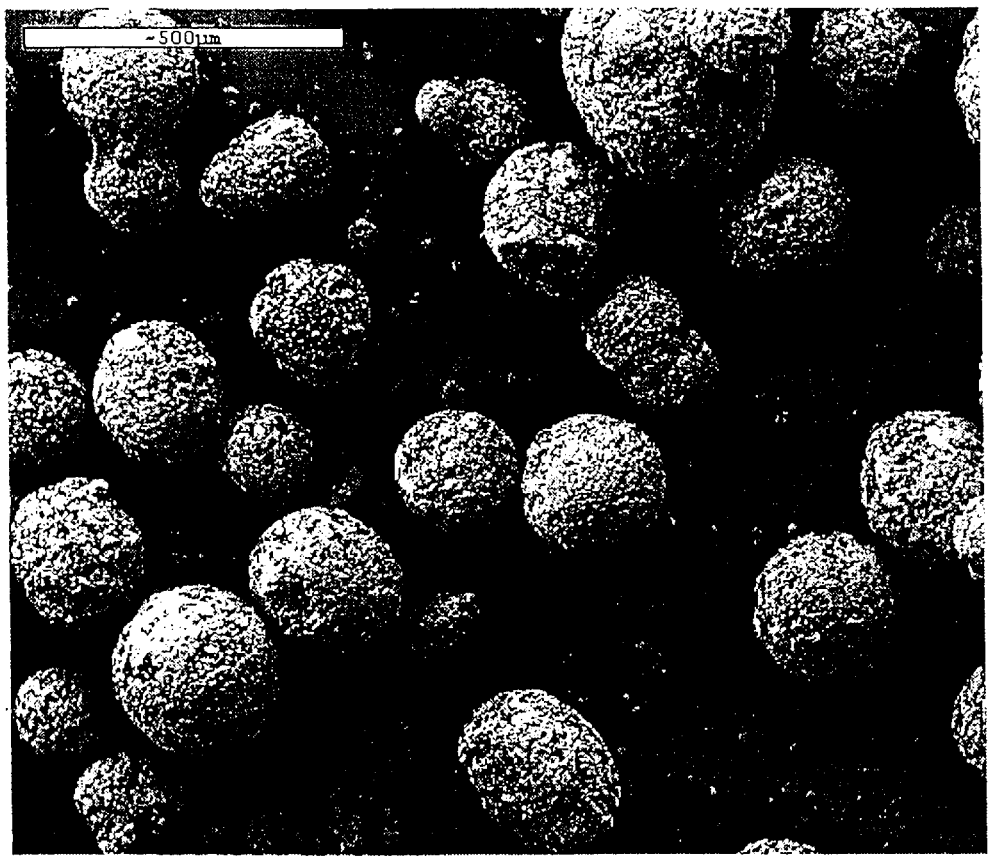
Figure 2 : 85 LACTOSE / 15 STARCH
MAGNIFICATION: X 85

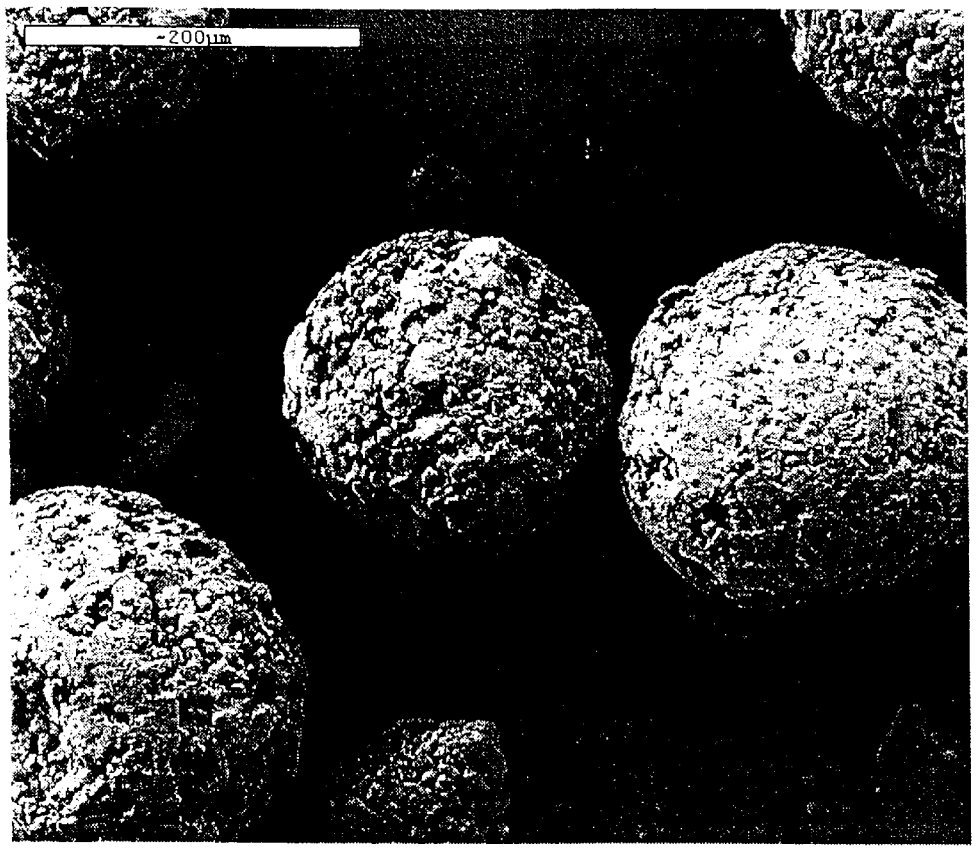
Figure 2' : 85 LACTOSE / 15 STARCH
MAGNIFICATION: X 225

GRANULES BASED ON STARCH AND LACTOSE

The subject of the present invention is a composition of granules based on starch and lactose, as well as the process which makes it possible to obtain these granules.

It also concerns the use of such granules in particular as excipient in the pharmaceutical industry or as additive or carrier in the food or chemical industries.

The pharmaceutical industry consumes many tons of starch and lactose. These are in particular used as excipients in dry formulations such as, for example, powders for filling hard capsules, powders to be dissolved, pulverulent nutrient preparations and tablets.

The food industry uses, for its part, this type of excipient in particular in foods and drinks to be dispersed and to be diluted.

As regards the field which is of particular interest for the present invention, namely pharmaceutical or food excipients, such excipients exist in the form of powders obtained by wet granulation of a mixture of lactose and starch, supplemented with binders or surfactants. These powders generally possess unsatisfactory direct tableting capacities.

The most important factors for assessing the direct tableting capacity of a powder are the flow capacity (regular supply to the tableting chamber from the hopper), the resistance to abrasion (or non-friability), and the cohesion after compacting of the particles, which determines the hardness of the tablets. The tablets produced must be sufficiently hard to withstand breaking but at the same time have good disintegration properties when they are in the gastric medium.

Among the excipients most commonly encountered in tableting, there may be mentioned in particular cellulose, starch, lactose and dicalcium phosphate.

Microcrystalline cellulose fulfils all the conditions expected of a direct tableting excipient, but it remains difficult to produce and is relatively costly. It has, in addition, the disadvantage of causing a decrease in the hardness of the tablets following uptake of water during storage. Additionally, it causes an unpleasant sensation in the mouth.

Lactose is a diluent which is widely used in tablet technology. It exists in two main forms: crystallized or spray-dried. Crystallized lactose exists in three different crystalline forms: anhydrous α-lactose (not commercially available), anhydrous β-lactose (usually referred to as anhydrous lactose) and α-lactose monohydrate. Anhydrous lactose has the disadvantage of being hygroscopic, which causes problems of stability over time. α-lactose monohydrate is stable but its tableting capacity and disintegration time remain inadequate. In order to improve the latter, lactose has been modified by spray drying and compression.

Spray-dried lactose is highly compressible, and the spherical shape of its particles allows good flow properties. It is less stable and its storage period is shorter than that of crystalline lactose. Tablets manufactured from spray-dried lactose develop a yellowish colour during storage which is more intense than that developed by lactose monohydrate.

Compressed lactose is a stable powder which flows well but is less compressible than spray-dried lactose. The tableting properties of lactose remain inadequate but they have been improved by addition of a binding or diluent excipient possessing better tableting capacity, such as a microcrystalline cellulose. These mixtures can be easily tableted by virtue of the addition of a lubricant. Microcrystalline celluloses have, however, the disadvantage of a high price, and of a reduction in the hardness of the tablets formed following moisture uptake.

As for starch, it has, because of the small size of its particles and its low density, the disadvantage of not flowing. The high elasticity of its granules make its tableting capacity inadequate to allow the manufacture of tablets of sufficient hardness. On the other hand, it possesses good disintegrating properties because of its swelling power in water. Starch can also serve as binder and diluent and even as flow-promoting agent.

It has been proposed to combine lactose and starch by wet granulation (BODE-TUNJI M. O., JAIYEOBA K. T., Labo-Pharma—Probl. Tech.—32, No. 340, March 1984, pp 190–192). However, it has been demonstrated that the addition of starch to lactose reduces the mean size of the granules and increases their friability, this effect being compensated for by the addition of a surfactant.

It has also been proposed to granulate lactose and starch using a synthetic polymer as binder (WAN L. C., LIM K. S., S.T.P. Pharma Sciences 1 (5) 285–293, 1991). The compositions obtained have an acceptable flow, but relatively low densities.

Processes for the preparation, by spray-drying, of complex tableting excipients, such as that described in U.S. Pat. No. 5,006,345, comprising lactose, a binder such as polyvinylpyrrolidone or hydroxypropylmethyl-cellulose, and a disintegrating agent such as in particular crosslinked carboxymethylcellulose or carboxymethylated starch, are also known.

A need therefore remains, which has not been satisfied, for a composition of lactose and starch granules possessing reduced friability, efficient flow, good tableting capacity and satisfactory disintegrating properties, while being only slightly hygroscopic.

The aim of the invention is to satisfy this need and the applicant has had the merit of finding, after numerous studies, that this aim can be achieved when granules in accordance with the invention, based on starch and lactose, are used. To obtain such granules, the applicant has observed that, against all expectations, it was advisable to use a granular starch and lactose mixture and to modify its physical characteristics by using an appropriate process such that moderate friability, satisfactory tableting capacity and efficient flow are obtained at the same time, while preserving the disintegrating properties.

The invention thus concerns granules consisting of lactose and starch, characterized in that they exhibit a friability of less than or equal to 80% according to a test A.

This test A consists in subjecting the granules to be tested to mechanical action in an apparatus called a friabilimeter. For this, an apparatus is used which is of the ERWEKA TA trademark manufactured by the company ERWEKA (GERMANY-6056 HEUSENSTAMM) revolving at a uniform rotating speed of 25 revolutions/minute, and equipped with a crushing chamber into which there are introduced 5 identical steel beads having a diameter of 17 mm and a weight of 18.87 g. To carry out this test A, a quantity of 15 g of product having a particle size between 100 and 200 μm is introduced into the crushing chamber of this friabilimeter and then the apparatus is rotated for 5 minutes.

At the end of the experiment, the proportion by weight represented by the residue retained on a sieve having a mesh width of 100 microns is determined.

The friability value corresponds to the percentage of powder not retained by the sieve defined above. The greater the percentage of powder not retained by the sieve, the greater the friability.

The granules in accordance with the invention exhibit, according to this test A, a moderate friability, that is to say of less than or equal to 80%, and preferably less than or equal to 60%.

The granules in accordance with the invention can also be characterized by a spherical structure when they are observed by scanning electron microscopy. This very specific structure is illustrated by FIGS. 1,1' and 2,2' which show the perfect sphericity of the granules obtained. FIG. 1 shows a scanning electron micrograph of a granule according to the invention having a lactose/starch ratio of 75/25. FIG. 2 shows a scanning electron micrograph of a granule according to the invention, having a lactose/starch ratio of 85/15. By virtue of this structure, the granules in accordance with the invention have a completely satisfactory flow.

According to one embodiment of the invention, the granules are characterized by a lactose to starch ratio of between 90/10 and 25/75. It is indeed possible to vary at will the proportions of lactose and starch in the granules in accordance with the invention, depending on the use which it is desired to make thereof.

"Lactose" is understood to mean lactose monohydrate as defined by the European Pharmacopoeia, 1997, 0187—p. 1111–1112. "Starch" is understood to mean natural or hybrid starches of any origin, of the granular type. Native maize starch is preferably used and, in particular, white maize starch such as that marketed by the applicant under the name "amidon extra-blanc" which makes it possible to obtain granules of completely satisfactory whiteness.

Above 90% of lactose relative to the starch contained in the granules, the applicant observed that the said granules did not possess satisfactory disintegrating properties. Below 25% of lactose, that is to say for more than 75% of starch in the granules, the latter can no longer be properly tableted because of the elastic properties of the starch and the flow properties are not satisfactory.

Preferably, a lactose to starch ratio of between 85/15 and 50/50 will be chosen.

According to another embodiment of the invention, the granules comprise lactose and starch and can, furthermore, contain any appropriate additive as long as it does not damage the desired properties of the final granules, such as in particular flavourings, colourings, stabilizing agents, disintegrating agents, binders, lubricants and preservatives. These may also be pharmaceutical or plant-protection active ingredients, or detergents.

The granules in accordance with the invention can be characterized by their tableting capacity determined according to a test B.

This test B consists in measuring the force, expressed in Newtons, which is representative of the tableting capacity of the composition of granules studied, given for two different values of density of tablets. This force represents the crushing resistance of tablets which are cylindrical with convex faces (radius of curvature of 14 mm), having a diameter of 13 mm, a thickness of 6 mm and apparent densities of 1.3 and 1.4 g/ml. This tableting capacity, expressed at such densities of tablets, represents the advantageous properties of the granules according to the invention for the purposes of direct tableting.

To carry out this test B, tablets are prepared from granules in accordance with the invention to which 0.5% by weight of magnesium stearate has been added beforehand as lubricant.

The tableting is performed by means of an AM type FROGERAIS alternating press. This press is equipped with round dies with concave faces, having a diameter equal to 13 mm.

The penetration of the top die and the filling volume of the bottom die are set on the press so as to vary the density of the tablets, and the corresponding hardness of these tablets is determined using an ERWEKA durometer of the TBH 30 GMD type.

The granules in accordance with the invention whose lactose to starch ratio is between 90/10 and 50/50 have a remarkable tableting capacity, superior to that of the prior art products, resulting in a tablet hardness greater than 70 N and preferably greater than 75 N for a density of 1.3 g/ml, and greater than 175 N and preferably greater than 180 N for a density of 1.4 g/ml.

The granules according to the present invention are characterized, in addition, by an angle of repose of less than 35°, preferably of less than 32°. The determination of the angle of repose of a powder is one of the most widely used methods for assessing its flow properties. It involves measuring the height of a cone formed by the powder which has flown out of a cylinder of known volume, and deducing therefrom the angle formed by this cone as a function of the radius of the cylinder used. The greater the angle formed, the poorer the flow of the powder. By way of example, the angles of repose of the excipients most generally used in direct tableting vary between 35 and 67°, the highest values being observed with celluloses and the lowest being observed with granulated products such as sorbitol or modified dicalcium phosphate. Spray-dried lactose generally exhibits an angle of repose of the order of 46° (as indicated by STAMM A. et MATHIS C., Labo-Pharma—Problemes et Techniques—N°252—Mars 1976). As for starch, it does not, so to speak, flow.

The granules in accordance with the invention possessing the characteristics mentioned above are capable of being obtained according to a multitude of variants, but most particularly according to a process characterized in that it comprises a step of spray-drying a suspension of lactose and starch. Surprisingly and unexpectedly, the applicant has observed that spray-drying applied to a suspension of lactose and native starch made it possible to obtain spherical granules possessing moderate friability, tableting capacity and efficient flow, while preserving disintegrating properties. This aim had so far not been achieved by means of the processes known to persons skilled in the art and which are applicable both to lactose and to starch. The latter indeed has a disadvantage when heat processes are used, which is the risk of cooking and thus losing its granular and therefore disintegrating character.

To carry out the spray-drying, a starch suspension is prepared in cold water, to which lactose monohydrate is added. The mixture, having a temperature normally between 15 and 25° C., is then spray-dried in a conventional spray-drier known to persons skilled in the art, generally choosing an inlet temperature of around 160° C. and a flow rate such that the temperatures of the air and of the spray-dried product are at around 65° C. at the outlet. Generally, an aqueous suspension of starch at 20% by weight will be used. The mixture may also comprise substances other than lactose and starch, as long as they are not subject to heat degradation. As regards the water content of the suspension containing the lactose and the starch, a dry matter content of 40 to 50% will generally be used. The lactose used is preferably in monohydrate form. As regards the starch, any granular starch is suitable. Maize starch, and preferably so-called "extra-blanc" maize starch such as that marketed by the applicant under this name will be advantageously chosen. The spray-dried powder can be used directly. It is provided in the form of perfectly spherical granules comprising co-spray-dried lactose and starch, and may thus be advantageously used as excipient, additive carrier or texturing agent in the food and pharmaceutical sectors. Many other applications of the granules in accordance with the invention can of course be envisaged because of the advantageous functional properties which they have, in particular in veterinary, plant-protection, and agricultural applications, as well as in the field of detergents.

The invention will be understood more clearly with the aid of the following examples and the FIGS. 1,1' and 2,2' relating thereto, which are intended to be illustrative and nonlimiting.

EXAMPLE 1

Preparation of Granules according to the Invention and Physical Characterization Various compositions of granules consisting of lactose and starch in ratios of 85/15, 75/25, 50/50 and 25/75 are prepared by co-spray-drying according to the invention. Lactose monohydrate and "extra-blanc" maize starch are used.

The principal physical characteristics of the compositions prepared are given in the following table, in comparison with products of the prior art.

|  | 25/75 | 50/50 | 75/25 | 85/15 | Native maize starch | Physical mixture of classic maize starch and lactose monohydrate |
|---|---|---|---|---|---|---|
| Mean diameter (μm) | 215 | 182 | 171 | 183 | 14 | 41 |
| Apparent density (g/l) | 0.6 | 0.6 | 0.58 | 0.59 | 0.43 | 0.44 |
| Tap density (g/l) | 0.65 | 0.65 | 0.69 | 0.70 | 0.74 | 0.82 |
| Flow time (s) | 3.7 | 3.8 | 4 | 5 | infinity | infinity |
| Angle of repose (°) | 30 | 28 | 33 | 38 | 55 | 52 |

The mean diameter is measured by an LS laser granulometer COULTER®, by the determination of the volumic repartition in granule size.

The apparent density is measured according to the pharmaceutical technical method 2.9.15 of the European Pharmacopoeia, 3rd edition.

The flow time is measured according to the pharmaceutical technical method 2.9.16 of the European Pharmacopoeia, 3rd edition.

The angle of repose is measured on a POWDER TESTER apparatus commercialized by HOSOKAWA, according to the method developed by Carr.

The granules according to the invention are provided in the form of dense powders, which is unexpected for spray-dried compositions. These powders have remarkable flow properties.

FIGS. 1,1' and 2,2'

The compositions of granules 75/25 and 85/15 as prepared in Example 1 are observed by scanning electron microscopy, and have a characteristic spherical structure.

EXAMPLE 2

Determination of the Tableting Profiles of the Granules according to the Invention A tableting profile is performed on the 50/50, 75/25 and 85/15 compositions, as well as on a spray-dried lactose composition of the prior art, in the following manner:

Tablets are prepared on an AM type Frogerais alternating press equipped with concave dies having a diameter of 13 mm, from a powder consisting of 99.5% of compositions of granules according to the invention and 0.5% of magnesium stearate.

Tablets having a thickness of 6 mm are obtained on which the density and the hardness on an ERWEKA durometer are determined. The disintegration time of the tablets is also determined, according to the method of the European Pharmacopea, $3^{rd}$ edition.

The results obtained are presented in the following table:

| COMPOSITION | Density | Mean hardness (N) | Disintegration time |
|---|---|---|---|
| 50/50 | 1.215 | 55 |  |
|  | 1.268 | 71 |  |
|  | 1.312 | 117 |  |
|  | 1.349 | 131 | 180 |
|  | 1.395 | 191 | 220 |
| 75/25 | 1.156 | 22 | 67 |
|  | 1.235 | 55 |  |
|  | 1.309 | 124 | 83 |
|  | 1.378 | 217 |  |
|  | 1.454 | 363 | 321 |
| 85/15 | 1.142 | 28 | 56 |
|  | 1.220 | 47 |  |
|  | 1.292 | 96 | 83 |
|  | 1.363 | 180 |  |
|  | 1.437 | 307 |  |
|  | 1.475 | 431 | 321 |
| Spray-dried starch | 1.100 | 33 | 60 |
|  | 1.253 | 101 |  |
|  | 1.333 | 181 | 261 |
|  | 1.403 | 313 |  |
|  | 1.481 | 463 | 1302 |

By drawing graphs of the tablet hardness as a function of their density, it is possible to determine the hardness obtained at density values of 1.3 and 1.4 according to test B:

|  | Hardness | | |
|---|---|---|---|
| Density | 50/50 | 75/25 | 85/15 |
| 1.3 | 104 | 116 | 105 |
| 1.4 | 197 | 259 | 244 |

EXAMPLE 3

Study of Storage Stability

In order to evaluate the stability of the tablets prepared from granules according to the invention, tablets are prepared with the preceding compositions of granules: 25/75, 50/50, 75/25, under the same conditions as Example 2.

The weight and the density of these tablets are measured and then these parameters are again measured after storing the tablets for 2 months at room temperature.

The variation in weight, expressed as a percentage, gives an indication of the level of hygroscopicity.

The variation in the hardness gives an indication of the stability of the tablets.

The following results are obtained:

25/75 COMPOSITION

| Initial data | | Variation after two months of storage | | |
|---|---|---|---|---|
| WEIGHT (mg) | HARDNESS (N) | WEIGHT | VARI-ATION HARDNESS | VARI-ATION |
| 786 | 78 | 787 | 0 | 77 | 0 |

50/50 COMPOSITION

| Initial data | | Variation after two months of storage | | |
|---|---|---|---|---|
| WEIGHT (mg) | HARDNESS (N) | WEIGHT | VARI-ATION HARDNESS | VARI-ATION |
| 564 | 75 | 580 | +2.8% | 83 | +11 |

75/25 COMPOSITION

| Initial data | | Variation after two months of storage | | |
|---|---|---|---|---|
| WEIGHT (mg) | HARDNESS (N) | WEIGHT | VARI-ATION HARDNESS | VARI-ATION |
| 729 | 81 | 734 | ≦1% | 72 | −11% |

EXAMPLE 4

Comparison between the Friability of the Granules according to the Invention and Those of the Products of the Prior Art A granulation of lactose and starch is performed on fluidized air bed according to the method described by WAN L. C. et LIM K. S., STP PHARMA SCIENCES 4 (560–570) 1988.

The 50/50 mixture according to the invention is granulated by pulverization of pure water ①, a solution of lactose ② and a solution of polyvinylpyrrolidone ③ which is the binder most often used in the pharmaceutical field, at a content of 5 g for 100 g of the composition according to the invention.

The friability is determined according to the previously described test A upon these three compositions as well as upon a composition of granulated lactose which is commercially available under the name TABLETTOSE® 80.

The results are demonstrated in the following table:

| COMPOSITION | Friability (test A) % |
|---|---|
| ① granulation with water | 100 (*) |
| ② granulation lactose | 100 (*) |
| ③ granulation PVP | 53 |
| 25/75 | 26 |
| 50/50 | 24 |

-continued

| COMPOSITION | Friability (test A) % |
|---|---|
| 75/25 | 48 |
| 85/15 | 52 |
| Tablettose ® 80 | 56 |

(*) the powder is so friable that the majority of the granules are destroyed during the preliminary sieving step between 100 and 200 μm.

It is surprising that the addition of starch which is reputed for increasing the friability of granules based on lactose has the opposite effect in the compositions according to the invention. The friability is as weak as that obtained by a conventional granulation process but with the addition of 5% of binder.

EXAMPLE 5

Study of the Shear Stability of Compositions according to the Invention

The compositions 75/25 and 85/15 prepared according to example 1 are mixed in an apparatus of the two-screw RUBERG type HM-50. The speed of the mixer is regulated at level 5. The volume of filling is at 30% for the 75/25 and 15% for the 85/15. The size of the particles of the tested composition is measured by seaving on successive of 32,63, 100,160,250 and 315 μm, before and after mixing for a period of 2, 5, 10, 15, 20 and 25 minutes.

The results are shown in the table below:

| | 75/25 | | | | | | |
|---|---|---|---|---|---|---|---|
| Particules size | % of composition as a function of mixing time (min) | | | | | | |
| | 0 | 2 | 5 | 10 | 15 | 20 | 25 |
| <32 μm | 2.6 | 2.9 | 3 | 3.7 | 3 | 4 | 3.3 |
| <63 μm | 6.1 | 6 | 6.2 | 6.9 | 7.9 | 6.6 | 6.6 |
| <100 μm | 10.4 | 10.6 | 11.6 | 10.7 | 12.3 | 11.2 | 10.4 |
| <160 μm | 23 | 23.4 | 24.7 | 23.5 | 24.7 | 23.7 | 22 |
| <250 μm | 65.3 | 66.4 | 66.6 | 65.7 | 67.6 | 65.5 | 64.7 |
| <315 μm | 9.1 | 90.8 | 91.4 | 91.6 | 93.2 | 91 | 90.4 |
| <400 μm | 99.5 | 99.2 | 99.7 | 99.8 | 99.6 | 99.9 | 99.9 |

| | 85/15 | | | | | | |
|---|---|---|---|---|---|---|---|
| Particules size | % of composition as a function of mixing time (min) | | | | | | |
| | 0 | 2 | 5 | 10 | 15 | 20 | 25 |
| <32 μm | 7 | 6.5 | 7.2 | 6.9 | 7.3 | 7.3 | 7.7 |
| <63 μm | 14.2 | 13.2 | 14.5 | 14 | 13.3 | 13.9 | 13.9 |
| <100 μm | 26.6 | 21.2 | 22.6 | 21.9 | 21.7 | 22.2 | 21.5 |
| <160 μm | 48.5 | 42 | 43.7 | 43.4 | 42.7 | 43.9 | 43.7 |
| <250 μm | 89 | 87.3 | 88.2 | 88 | 88 | 88.2 | 88.6 |
| <315 μm | 99.2 | 99.1 | 99.1 | 99 | 99.1 | 99.1 | 99.1 |

There is no modification of the granulometry of the compositions during the mixing. The two screws of the mixer do not break the powder, because there is no formation of fines. This confirms the low friability of the compositions according to the invention, illustrated by their good stability to shearing.

What is claimed is:

1. Spherical granules consisting of co-spray-dried lactose and granular starch, wherein the lactose/starch ratio is between 90/10 and 25/75, said granules having a friability of less than or equal to 80%, according to a test A.

2. Granules according to claim 1, having a friability of less than or equal to 60% according to test A.

3. Spherical granules according to claim 1, wherein the lactose/starch ratio is between 85/15 and 50/50.

4. Spherical granules consisting of co-spray-dried lactose and granular starch, having a friability of less than or equal to 80% according to a test A, and presenting a lactose to starch ratio of between 50/50 and 90/10, having a tableting capacity, determined according to a test B, of greater than or equal to 70 N, for a tablet density of 1.3 g/ml and greater than or equal to 170 N, for a tablet density of 1.4 g/ml.

5. Spherical granules according to claim 4 wherein the tableting capacity is greater than or equal to 80 N for a tablet density of 1.3 g/ml and greater than or equal to 180 N for a tablet density of 1.4 g/ml.

6. Spherical granules according to claim 1, having an angle of repose of less than 45°.

7. Spherical granules according to claim 6 having an angle of repose of less than 40°.

8. Process for the preparation of spherical granules consisting of lactose and granular starch, in a lactose/starch ratio between 90/10 and 25/75, comprising the steps of preparing an aqueous suspension of granular starch, adding lactose to said starch suspension, spray-drying the resulting suspension.

9. Process according to claim 8, wherein the lactose/starch ratio is between 85/15 and 50/50.

10. Spherical granules according to claim 4, having an angle of repose of less than 45°.

11. Spherical granules according to claim 10 having an angle of repose of less than 40°.

* * * * *